(12) United States Patent
Kumakhov et al.

(10) Patent No.: US 7,149,279 B2
(45) Date of Patent: Dec. 12, 2006

(54) DETECTING UNIT FOR X-RAY DIFFRACTION MEASUREMENTS

(75) Inventors: Muradin A. Kumakhov, Moscow (RU); Nariman S. Ibraimov, Moscow (RU); Alexander V. Lyuttsau, Moscow (RU); Ekaterina V. Likhushina, Moscow (RU); Alexander E. Bulkin, Moscow (RU); Svetlana V. Nikitina, Moscow (RU)

(73) Assignee: Institute for Roentgen Optics, Moscow (RU)

( * ) Notice: Subject to any disclaimer, the term of this patent is extended or adjusted under 35 U.S.C. 154(b) by 45 days.

(21) Appl. No.: 10/865,939

(22) Filed: Jun. 14, 2004

(65) Prior Publication Data

US 2005/0041776 A1    Feb. 24, 2005

(30) Foreign Application Priority Data

Aug. 19, 2003   (RU) ............................ 2003125341

(51) Int. Cl.
 *G01N 23/20*    (2006.01)
(52) U.S. Cl. .......................................... 378/71; 378/84
(58) Field of Classification Search ................ 378/149, 378/70, 84, 73, 78, 80, 186, 71
 See application file for complete search history.

(56) References Cited

U.S. PATENT DOCUMENTS

| | | | | |
|---|---|---|---|---|
| 3,833,810 A | * | 9/1974 | Efanov et al. ................. | 378/74 |
| 4,495,636 A | * | 1/1985 | Jacobs et al. .................. | 378/87 |
| 4,958,081 A | * | 9/1990 | Malmin et al. .......... | 250/505.1 |
| 5,373,544 A | * | 12/1994 | Goebel ......................... | 378/71 |
| 5,727,044 A | * | 3/1998 | Fraser et al. ................. | 378/149 |
| 5,739,542 A | * | 4/1998 | Sudo et al. ............... | 250/483.1 |
| 5,744,813 A | * | 4/1998 | Kumakhov ............... | 250/505.1 |
| 5,812,631 A | * | 9/1998 | Yan et al. ...................... | 378/85 |
| 5,933,473 A | * | 8/1999 | Kitaguchi et al. ............ | 378/57 |
| 6,069,934 A | * | 5/2000 | Verman et al. ................ | 378/73 |

FOREIGN PATENT DOCUMENTS

RU    2096353    11/1997

OTHER PUBLICATIONS

Mildner, D.F.R, et. al. "A monolithic polycapillary focusing optic for polychromatic neutron diffraction applications" Review of Scientific Instruments, vol. 73., No. 5, May 2002, pp. 1985-1993.*

(Continued)

*Primary Examiner*—Edward J. Glick
*Assistant Examiner*—Hoon Song
(74) *Attorney, Agent, or Firm*—McDermott Will & Emery LLP

(57) ABSTRACT

Detecting unit comprises position-sensitive detector 1 and collimating system 2, situated in front of its window 19. Collimating system being made in the form of honeycomb structure comprising multitude of tubular channels for transmittance of diffracted X-ray radiation. Walls of adjacent tubular channels are fused together. Outlet ends of the channels, forming outlet end face 22 of the collimating system, are oriented towards window 19 of the position-sensitive detector. Outlets of the channels in outlet end face of the collimating system 2 are arranged in several rows along window 19 of the position-sensitive detector 1. Walls of the tubular channels are formed from material absorbing X-ray radiation. Collimating system 2 is installed with possibility of adjusting its position relative to the window 19 alignment of the position-sensitive detector. The embodiment specified provides for prevention of the difractograms distortion and the increase of sensitivity of the detecting unit.

12 Claims, 16 Drawing Sheets

OTHER PUBLICATIONS

Figure 1A:
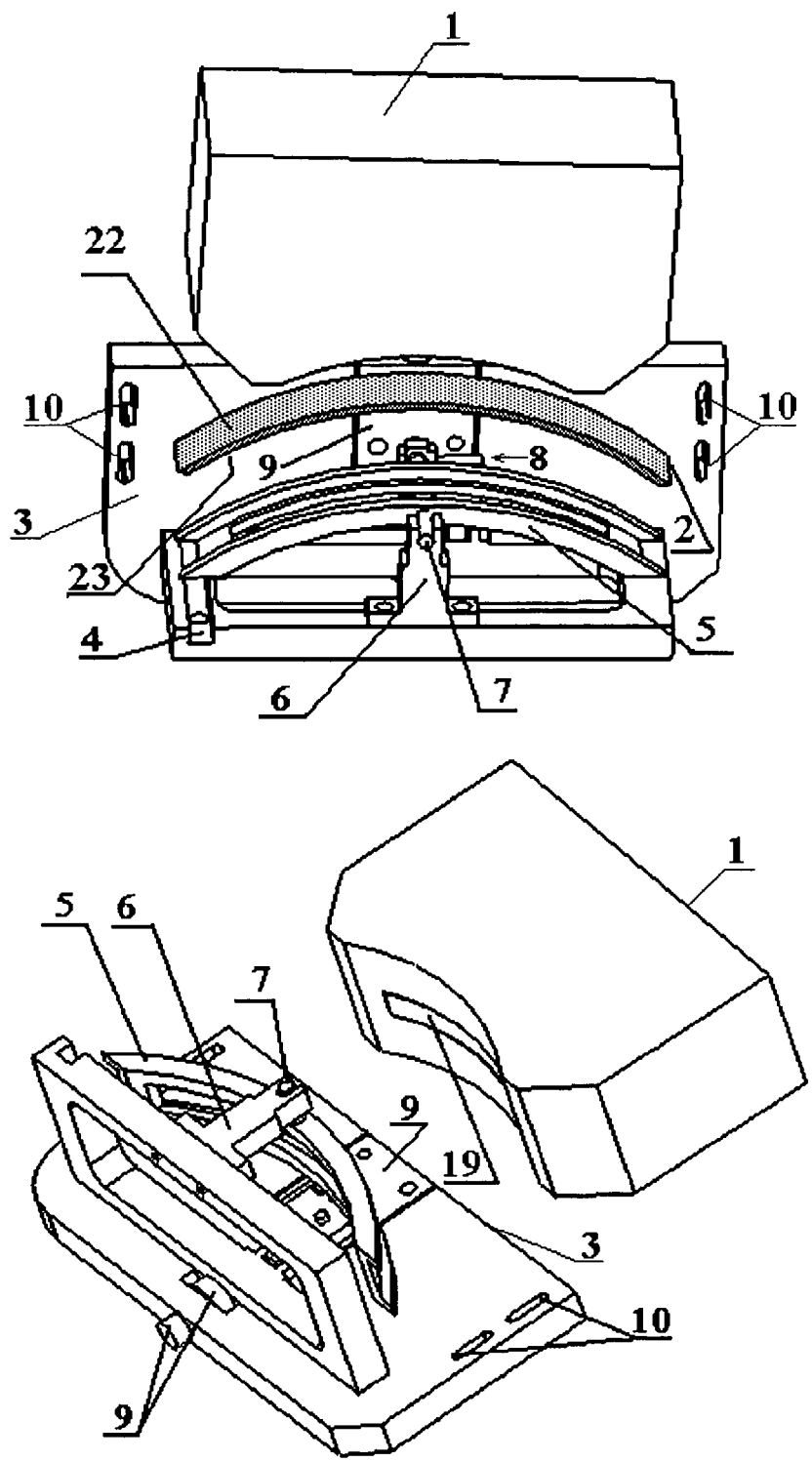

D.A. Goganov, et al., Sealed-off proportional X-ray emission counter SPRO-12.—In: Apparattura I methody rentgenovskogo analiza (Equipment and methods for X-ray analysis). Leningrad, Mashinostroenie editing house, 1972, Issue 11, pp. 151-155 (in Russian).

D. Ortendahl et al., "One dimensional curved wire chamber for powder X-ray crystallography", Nucl. Instrum. And Meth., 1978, vol. 156, No. 1-2, pp. 53-56.

Your Partner in X-ray Diffraction, STOE News, STOE&CIE, 2003, S. 1-28.

K. Omote et al., "A Convergent Beam, Parallel Detection X-Ray Diffraction System for Characterizing Combinatorial Epitaxial Thin Films", The Rigaku Journal, vol. 18, No. 1, 2001, pp. 38-45.

S.S. Gorelik, et al., "Rentgenovskiy i elektronno-opticheskiy analiz (X-ray and electron-optical analysis)", Moscow, MISIS, "Nauka" publishers, 2002, pp. 117-122 (in Russian).

D.K.Bowen et al., "High-resolution X-ray diffractometry and topography", Sankt-Peterburg, Nauka publishers, 2002, pp. 31-60, 95-96 (Russian translation).

V. Kahenberg et al., "Crystal structure analysis of sinthetic $Ca_4Fe\,1,5Al7,67O32$: A high-pressure, spinel-related phase, American Mineralogist", 2001, vol. 86, pp. 1477-1482.

* cited by examiner

DETECTING UNIT FOR X-RAY DIFFRACTION MEASUREMENTS

The invention relates to means used in conducting X-ray diffraction measurements, in particular, those belonging to X-ray diffractometers, namely, to a detecting unit.

A detecting unit is known, which comprises detector and Soller slit system in the form of assembly of thin plates parallel to a plane, is comprised the primary X-ray beam and the normal to surface of the sample studied, that also passing through center of goniometer (see D. A. Goganov, B. S. Losinsky, N. B. Tsvetova, T. P. Toporkova. Sealed-off proportional X-ray emission counter SPRO-12.—In: Apparatura i metody rentgenovskogo analiza (Equipment and methods for X-ray analysis). Leningrad, Mashinostroenie editing house, 1972, Issue 11, pp. 151–155 [1] (in Russian)). This detecting unit also comprises a collimating slit, located in a plane perpendicular to that specified and carrying a beam of X-rays reflected by the sample studied. The largest dimension of irradiated area of the sample studied lies in the plane passing through collimating slit in parallel with its generatrices, and the smallest one—in the plane perpendicular to collimating slit. Crystallographic, Bragg "reflections" take place according to fundamental equation of diffraction: $2d \sin \Theta = n\lambda$, where d denotes interplanar spacings in "the reflecting" planes system, $\Theta$ is angle of reflection, n is order of reflection, and $\lambda$ denotes wavelength of incident radiation. However, due to finite dimensions of the area irradiated, not only multiple reflections become possible, but also reflections from other plane systems of coherent scattering regions. These planes are located not parallel to the surface of the sample studied and can generate reflected beams from some other geometrical points of irradiated area, located at different angles to the collimating slit region. In the plane located perpendicular to collimating slit, task of extraneous rays selection is accomplished by collimating slit, and in the parallel plane—by Soller slit.

This detecting unit, utilized in X-ray diffractometric photography with focusing schemes, captures only narrow beam of X-rays reflected by the sample studied. In real measurements, this angle is of an order of several angular minutes. In order to obtain information with such detecting unit in angular range of several tens of degrees, it is necessary to perform exposure several hundred times. Total exposure time will increase correspondingly.

There is also known a detecting unit for X-ray diffraction measurements according to non-focusing scheme using parallel beam technique. This detecting unit comprises straight or curved position-sensitive detector and a slit situated along detector window (see Ortendahl D., Perez-Mendez V., Stoker J. One dimensional curved wire chamber for powder X-ray crystallography.—Nucl. Instrum. and Meth., 1978, Vol. 156, No. 1–2, p. 53–56, [2]).

Due to the fact of this detecting unit have the detector extended along diffraction angle, in case of its utilization in the above scheme of measurements; the information is obtained simultaneously for a certain range of reflection angles $\Theta$.

However, collimating system, such as represented by said slit, is narrows considerably the detector window in the plane perpendicular to the diffraction angle, thus lead to reducing reflected radiation intensity being detected. At the same time, the collimation is completely absent in the plane of the diffraction angle. As a consequence, any reflected X-rays, incident on detector, are captured, resulting in distortion of the diffractogram obtained.

Detecting unit for X-ray diffraction measurements, known from [2], is the most close to that proposed.

The invention proposed is directed to achievement of technical results involving the prevention of distortion in the diffractograms obtained and also increase the detecting unit sensitivity. Below, in disclosure of the technical substance of the detecting unit proposed and by description of its particular embodiments, other kinds of technical result achieved will be identified as well.

The proposed detecting unit for X-ray diffraction measurements, similar to that most close, known from [2], comprises position-sensitive detector and collimating system located in front of its window.

In order to achieve technical result mentioned, collimating system in the detecting unit proposed, as distinct from said the closest solution, known from [2], is made in the form of honeycomb structure, comprising multitude of tubular channels for conveying the diffracted X-ray radiation. The walls of adjacent tubular channels are fused together. Tubular channels, forming outlet end face of collimating system, are oriented with their outlet ends, towards window of the position-sensitive detector, and are made converging towards inlet end face of the collimating system. At that, outlets of tubular channels in the outlet end face of collimating system are arranged in several rows along window of the position-sensitive detector. Walls of the tubular channels are made of material capable to absorb X-ray radiation, or have a coating of such material.

In particular, tubular channels may have the shape of a truncated cone or pyramid.

An embodiment of the proposed detecting unit is possible, in which case of the greatest transverse dimension D of a separate tubular channel of the collimating system and its length H are satisfied relationship: $D/H > \theta_c$, where $\theta_c$ denotes critical angle of total external reflection of X-ray radiation from channel walls material. Fulfilment of this condition prevents possibility of transmittance to the channel outlet of rays, having at the tubular channel inlet a deviation from its longitudinal axis below $\theta_c$, due to multiple total external reflections.

The detecting unit may be structured with collimating system having outlet end face in the form of cylindrical surface, with tubular channels oriented by radii of this cylindrical surface.

The inlet end face of collimating system of the detecting unit proposed may also have a shape of cylindrical surface, coaxial with that specified above.

In these cases collimating system has a linear focus situated on axis of the specified cylindrical surfaces.

The collimating system of the detecting unit may be constructed also with planar parallel to one another surfaces of outlet or inlet end faces and longitudinal axes of tubular channels having extensions intersecting in a point (a focus of collimating system), laying on the perpendicular to said planar surfaces, and passing through geometrical center of outlet or inlet end faces.

In another particular embodiment, collimating system may be executed with planar surfaces of outlet and inlet end faces, situated in parallel one to another, and longitudinal axes of tubular channels oriented by radii of coaxial cylindrical surfaces which axis is the linear focus of the collimating system.

The particular embodiments, which were described above, define a wide range of engineering possibilities in the course of manufacturing the detecting unit proposed, equipped with collimating system in the form of honeycomb structure having tubular channels, fused together by their walls.

The tubular channels may be formed using glass mono- or polycapillaries.

At that, their walls may be made, in particular, from lead glass.

Walls of the tubular channels, formed by glass mono- or polycapillaries, may have a coating of lead or other heavy metal.

Collimating system of the detecting unit proposed is installed with possibility of adjusting its position relative to window of the position-sensitive detector. Changes in distance or orientation of the collimating system in respect to detector window allow to adjust position of focus (a point of intersection, or line segment intersecting with extensions of longitudinal axes of the tubular channels of collimating system in the embodiments described above) relative to surface of the sample studied, as well as to display interference pattern of diffraction in a form typical for different methods of its capture. This, in its turn, provides possibility to compare diffractograms obtained with those containing in different databases collected in X-ray diffraction pictures.

In particular, collimating system may be installed with possibility of linear displacement in the direction of longitudinal axis of one of its tubular channels, situated in central zone of the collimating system.

Collimating system may be installed also with possibility of rotation about axis, perpendicular to a plane passing through the middle one of tubular channels rows having outlets situated in the outlet end face of the collimating system.

It may be installed also with possibility of rotation about axis lying in a plane passing through the middle one of tubular channels rows having outlets situated in outlet end face of the collimating system, and perpendicular to central tubular channel in said row.

The existence of possibility for said rotation of collimating system allows to transmit selectively reflected X-rays in different angular ranges with different collimation, depending on objectives of investigation, without changing mutual angular position of interference maxima's centers of gravity, but with changing and redistributing intensity between them.

Figure 1B:
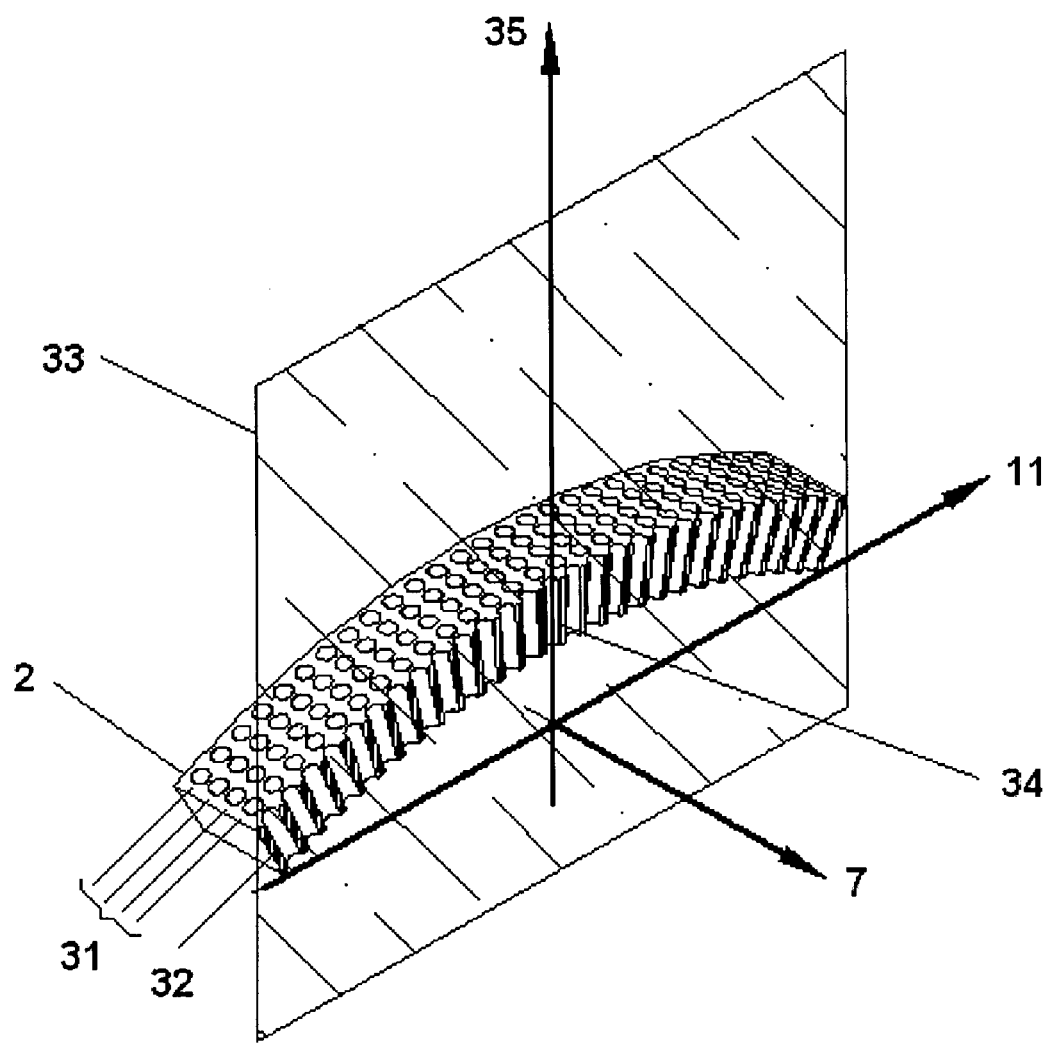
Figure 2:
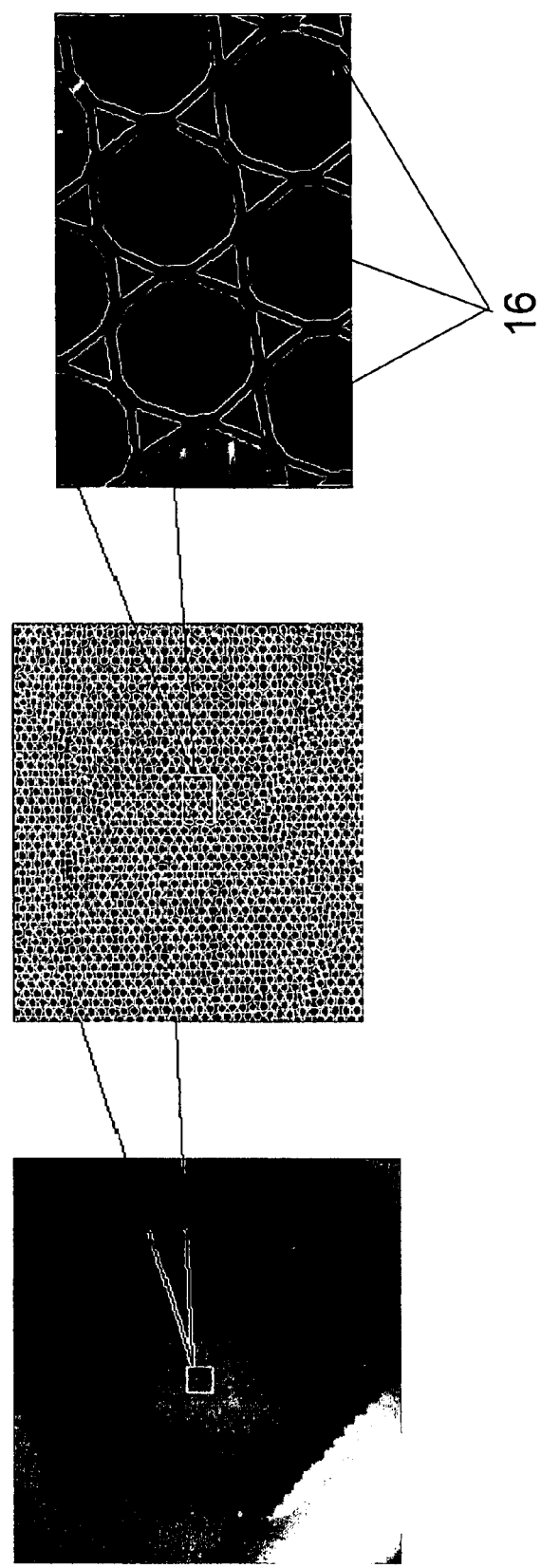
Figure 3:
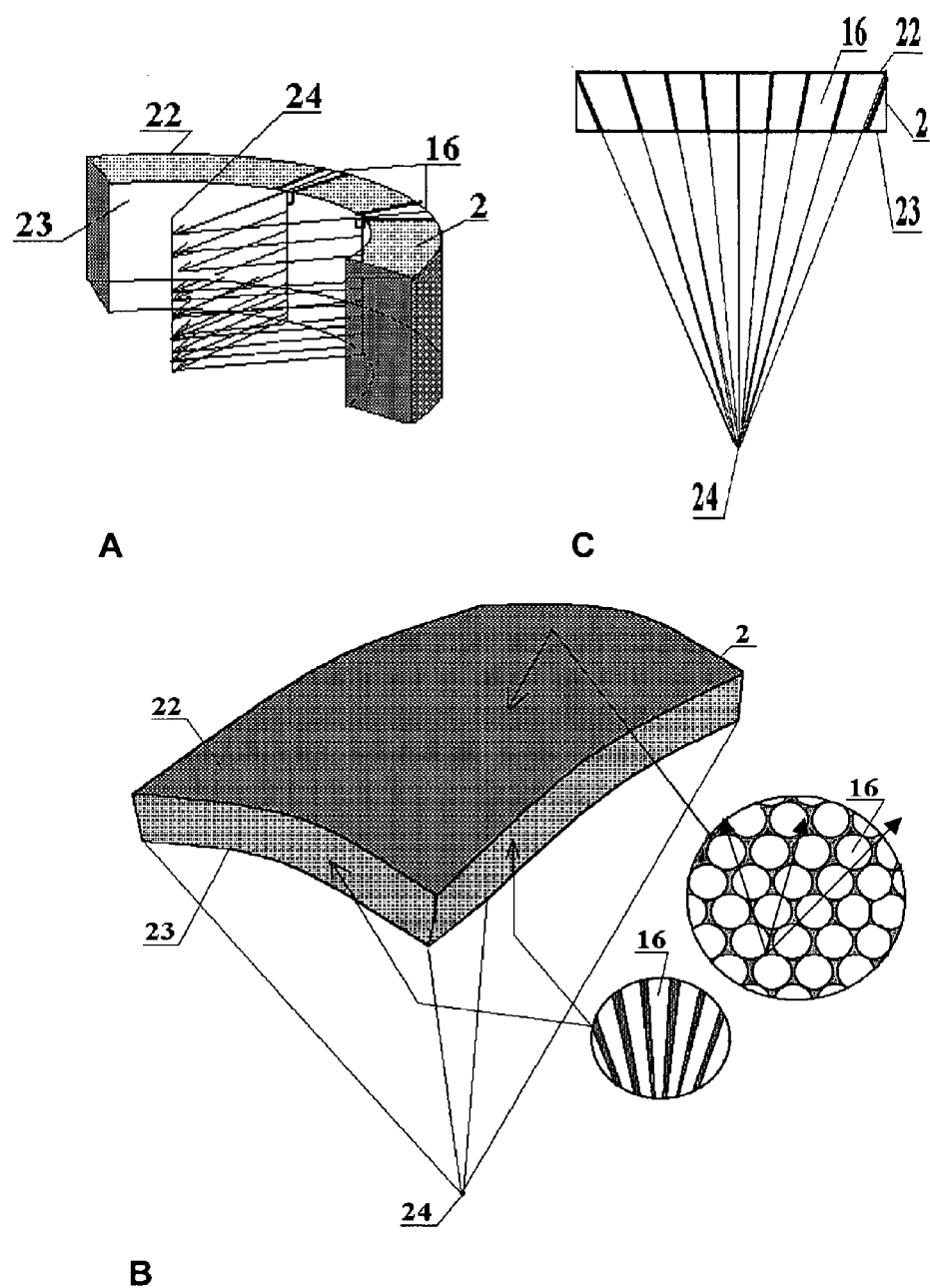
Figure 4:
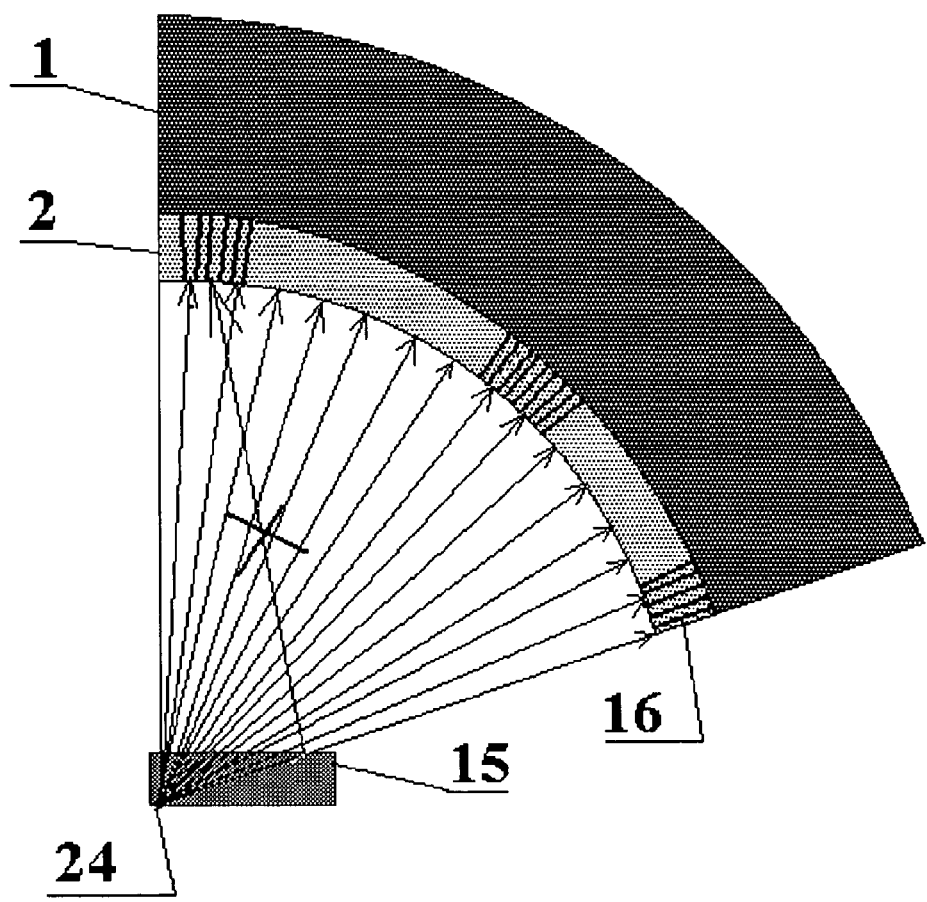
Figure 5:
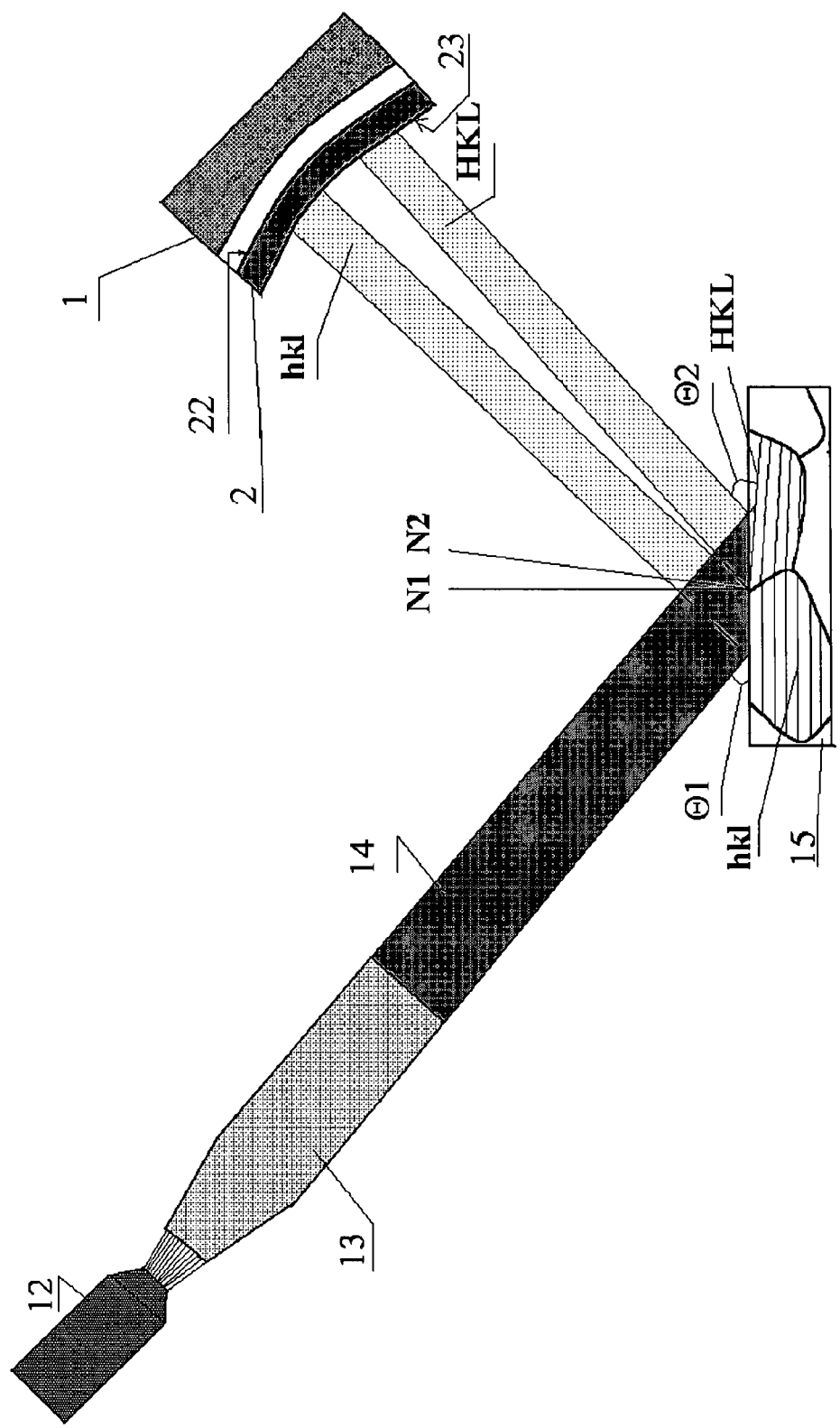
Figure 6:
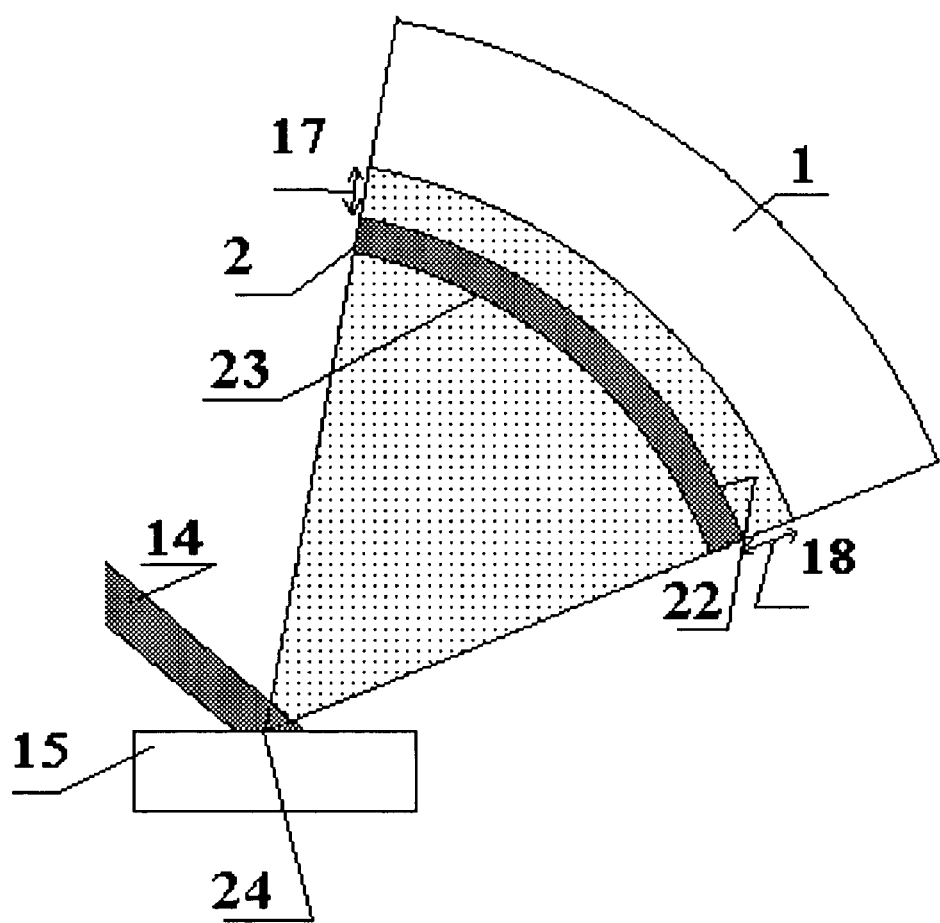
Figure 7:
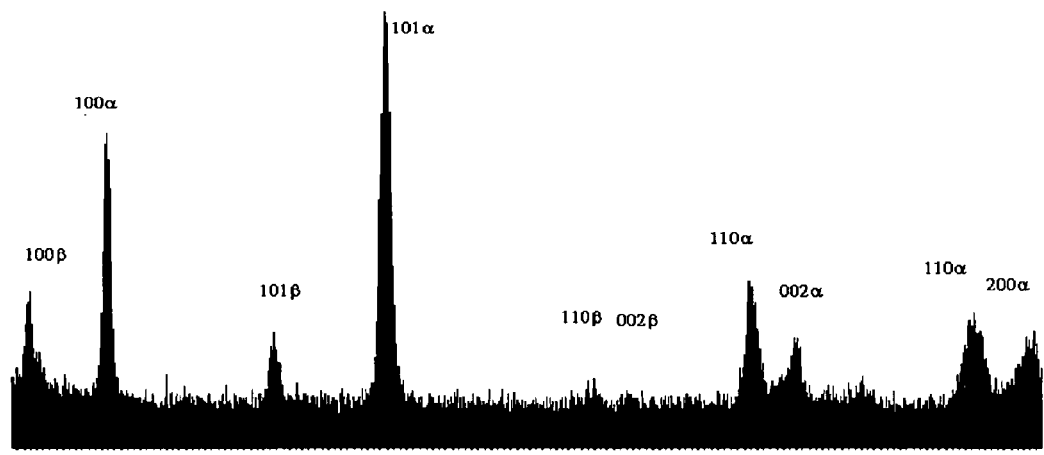
Figure 7:
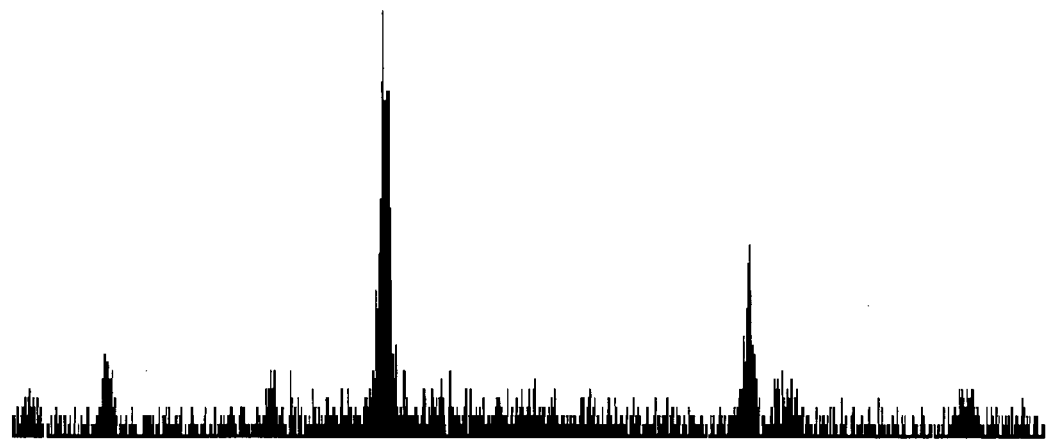
Figure 8:
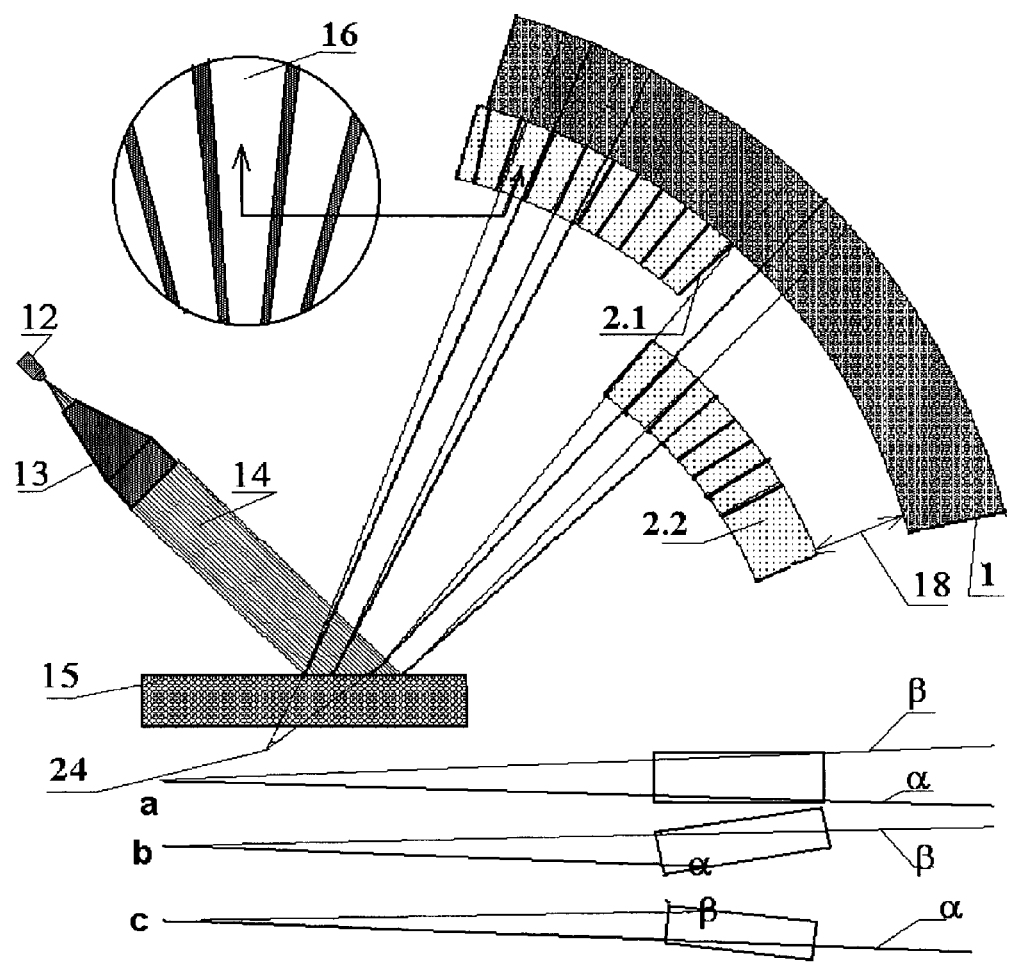
Figure 9:
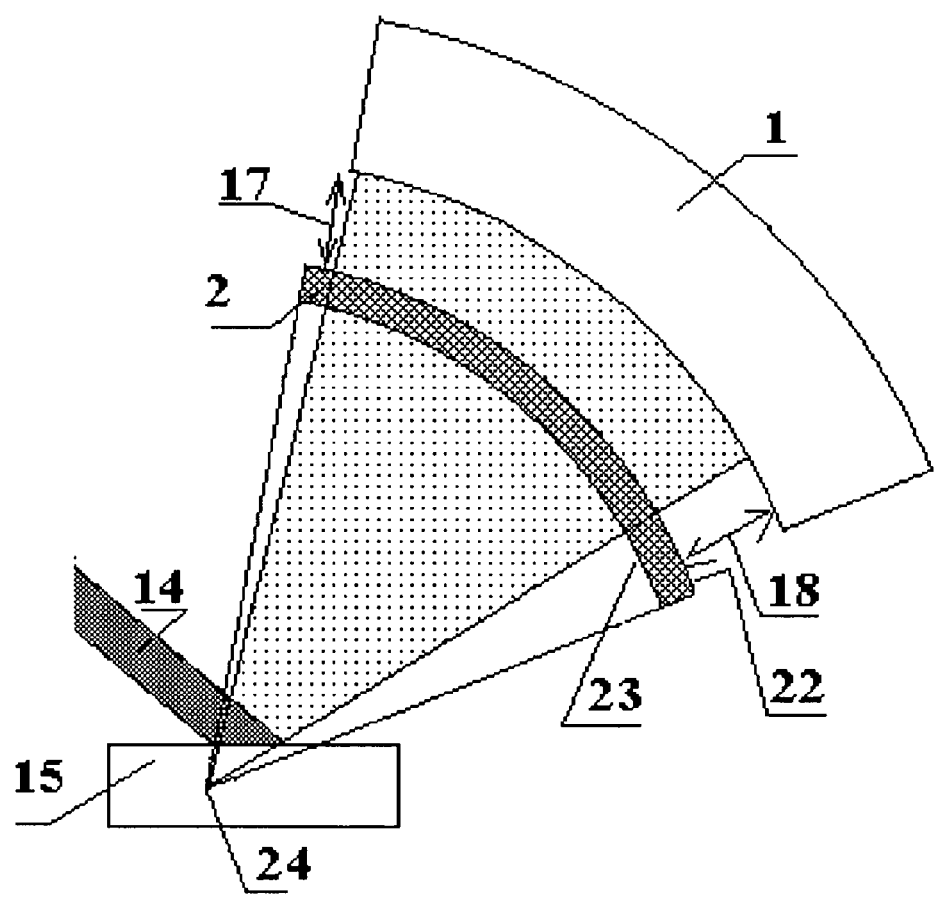
Figure 10:
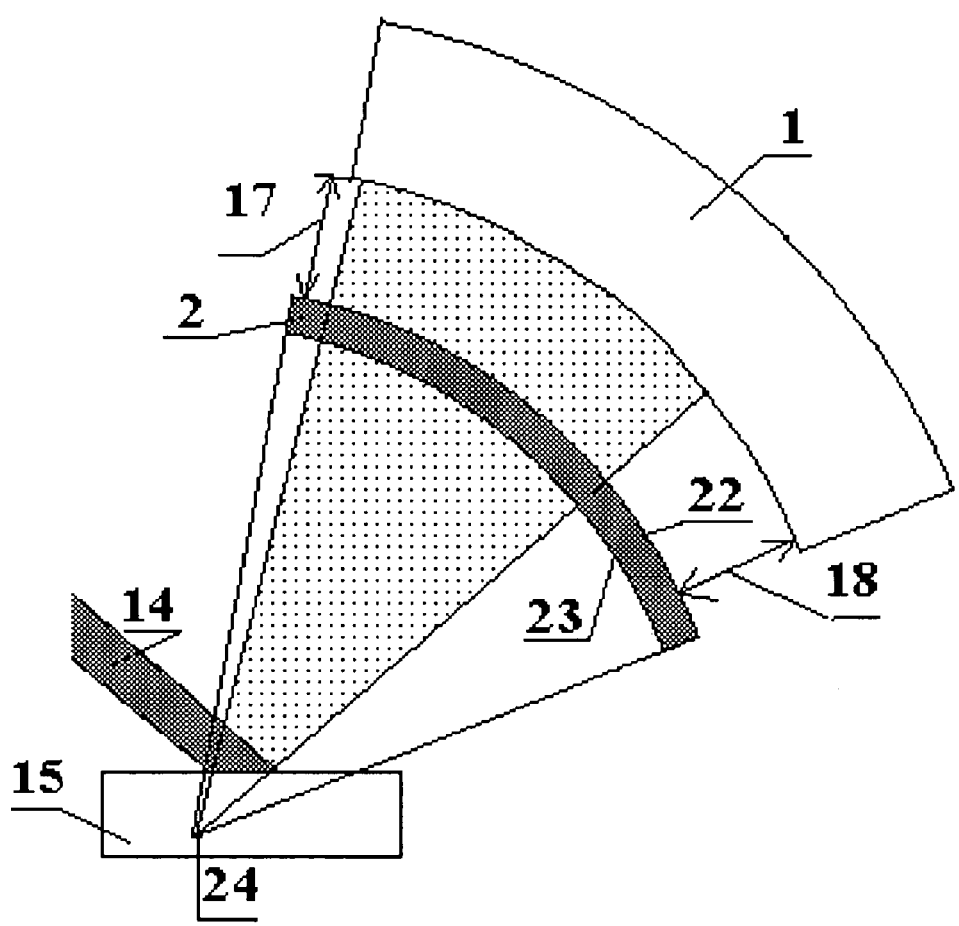
Figure 11:
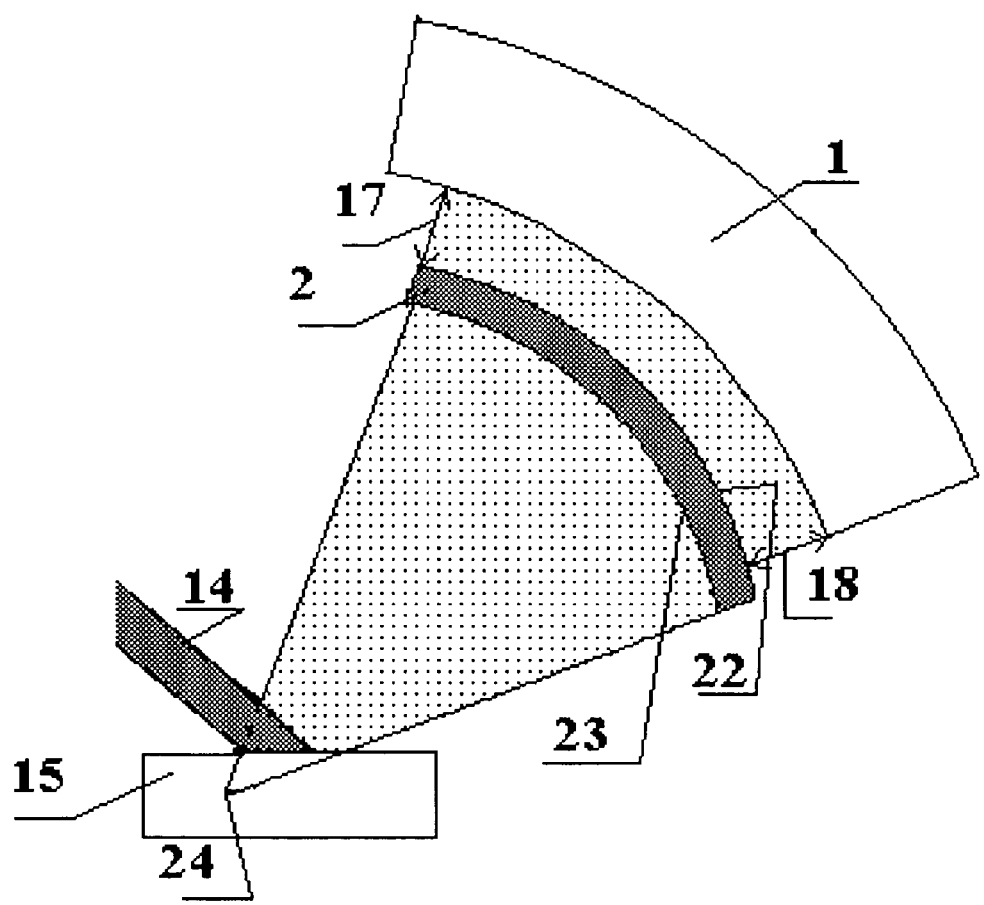
Figure 12:
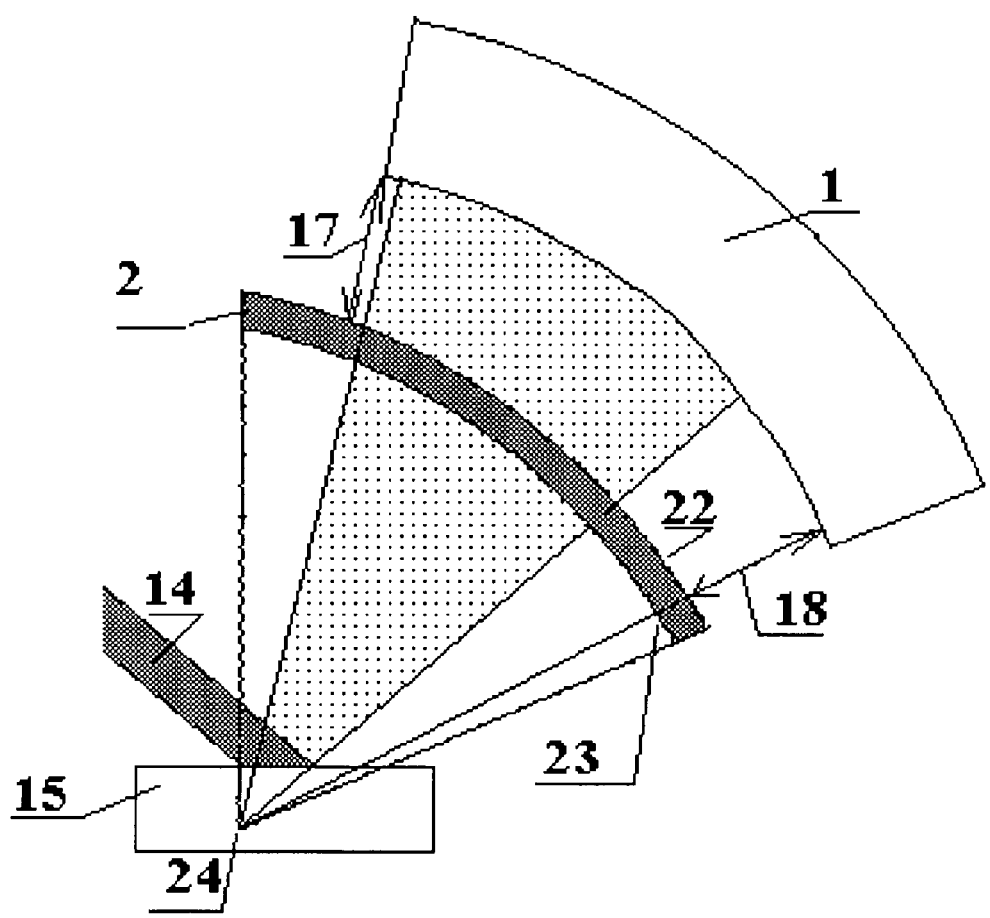
Figure 13:
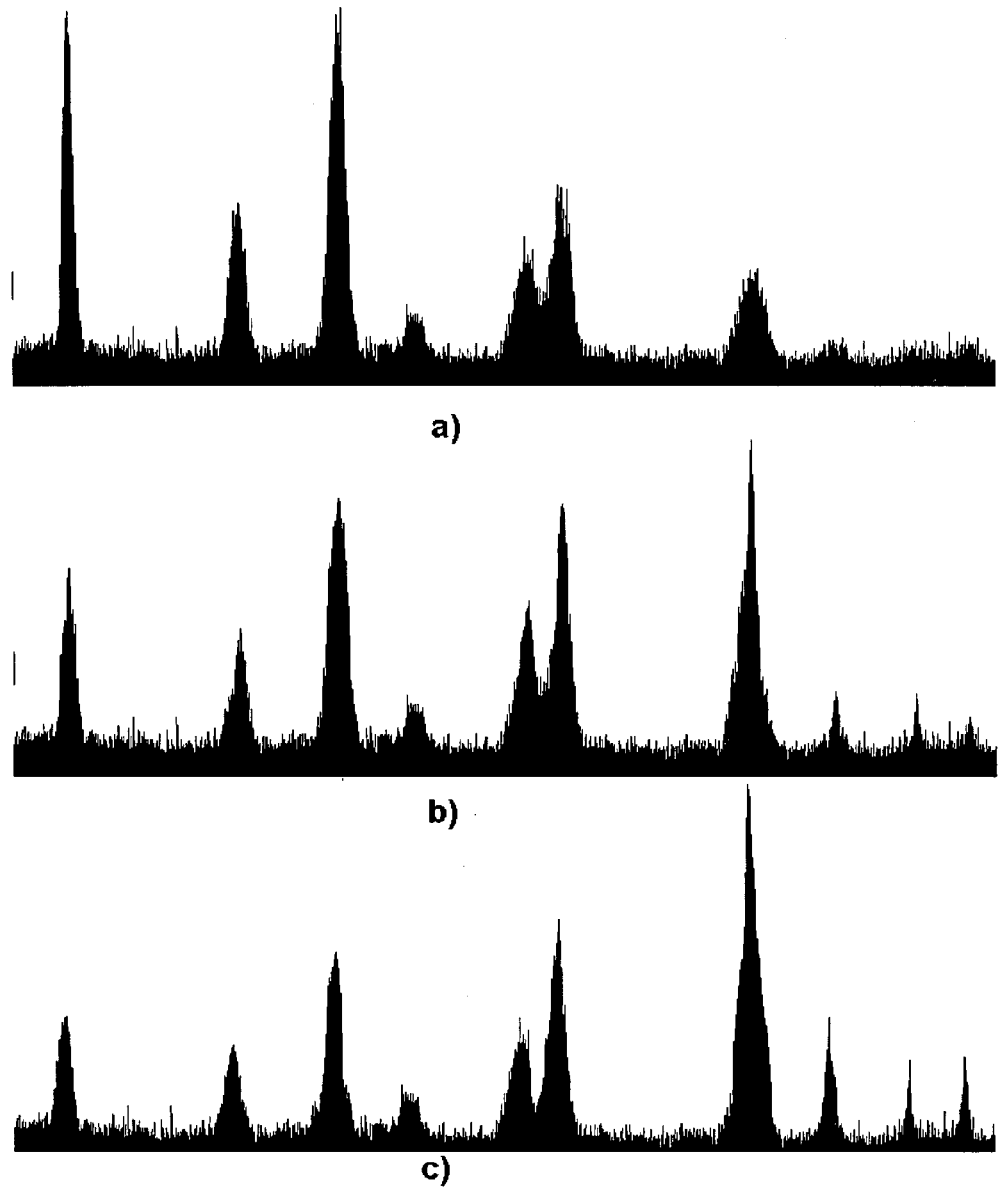
Figure 14:
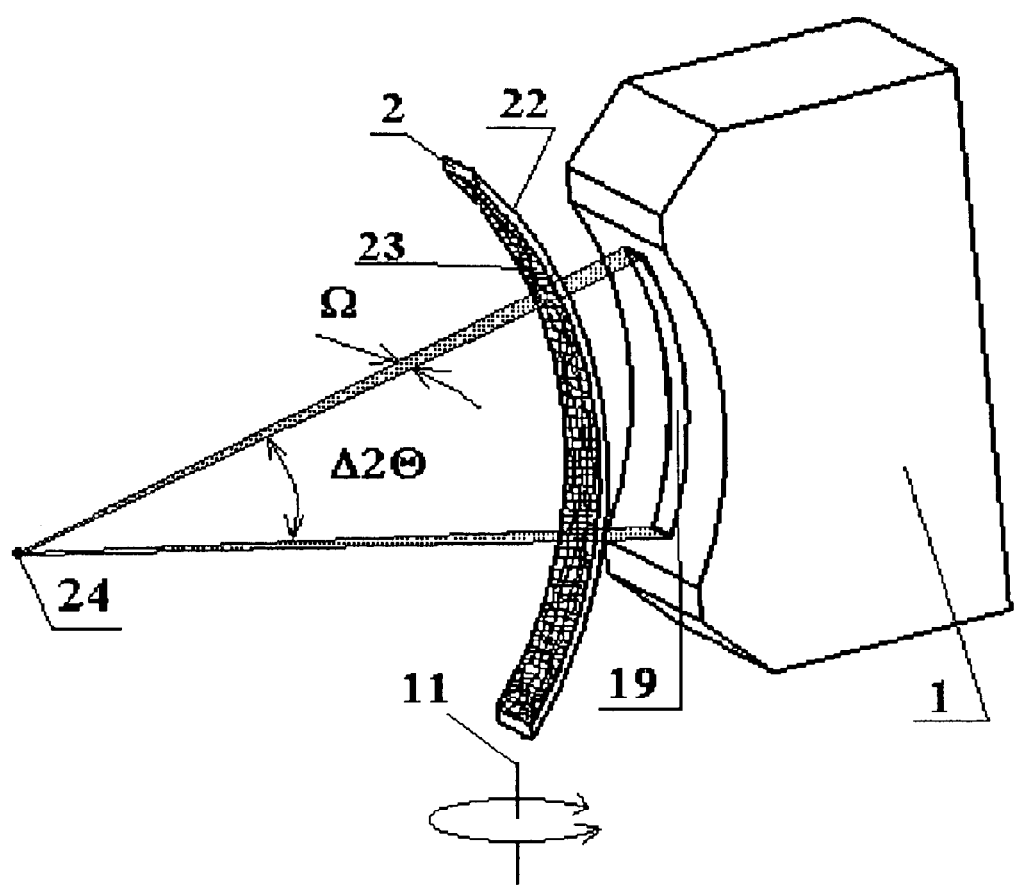
Figure 15:
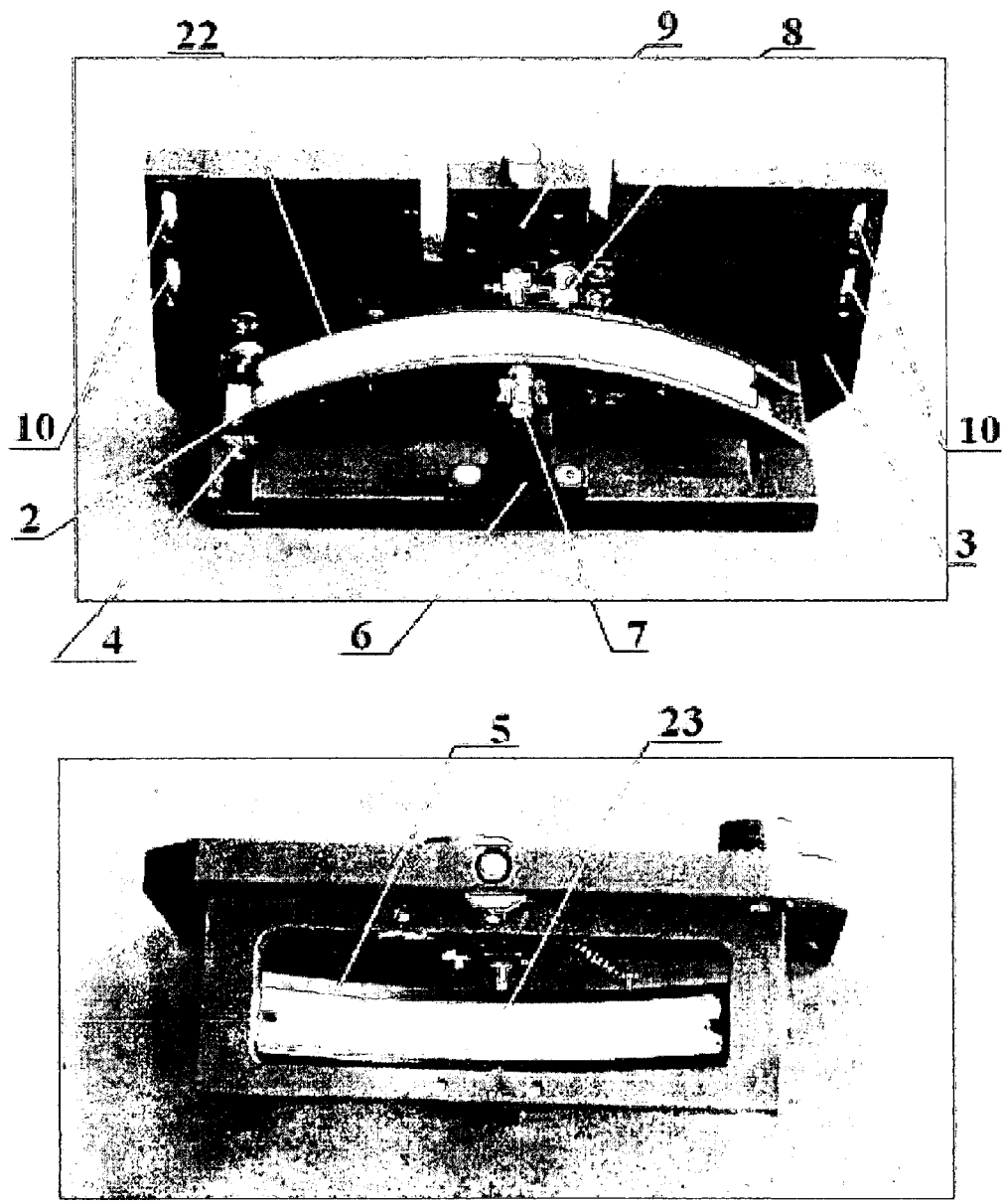

The detecting unit proposed for X-ray diffraction measurements is illustrated with drawings, which show:

in FIG. 1A—schematic view of the device proposed;
in FIG. 1B—collimating system;
in FIG. 2—graphical representation of collimating system structure at different magniifcation;
in FIG. 3—fragments of collimating system having different shape;
in FIG. 4—collimating system positioned in front of detector window;
in FIG. 5—procedure of measurements to record diffractogram by parallel beam method;
in FIG. 6—arrangement of collimating system focused on surface of the sample studied;
in FIG. 7—tungsten carbide (WC) diffractograms;
in FIG. 8—selective transmission of rays by collimating system depending on its position in front of detector;
in FIG. 9—displacement of collimating system in the direction of longitudinal axis of one of the tubular channels;
in FIG. 10—further displacement of the collimating system relative to that shown in FIG. 9;
in FIG. 11 and FIG. 12—rotations of collimating system about axis 7 (FIGS. 1A, 1B);
in FIG. 13—change in intensities ratio of diffraction peaks depending on angular position of collimating system;
in FIG. 14—rotation of collimating system about axis 11 (FIG. 1B);
in FIG. 15—photographs of collimating system on mounting plate with mechanisms for its displacement and rotation relative to the position-sensitive detector.

Proposed detecting unit for X-ray diffraction measurements comprises following elements (FIG. 1A):

position-sensitive detector 1;
collimating system 2 (shown only on upper projection in FIG. 1A), rigidly mounted on rocker 5, which applicability is mentioned below;
mounting plate 3 for sliding joint with position-sensitive detector 1 in slotted guides 10 by means of mechanism 9 and arrangement of other mechanisms on said plate;
mechanism 4 for rotation of collimating system 2 about axis 7 perpendicular to a plane passing through the middle one of tubular channels rows (see also FIG. 1B);
rocker 5, used for mounting of the collimating system in mechanism for its rotation around axis 7 and for rotation of said mechanism itself about axis lying in a plane passing through the middle one of tubular channels rows, perpendicular to the central tubular channel in said row (axis 11 in FIG. 1B);
frame 6 for mounting of axis 7 on mounting plate 3;
mechanism 8 for rotation of collimating system 2 around above mentioned imaginary axis 11 (see FIG. 1B) lying in a plane passing through the middle one of tubular channels said axis being perpendicular to the central tubular channel in the middle of row;
mechanism 9 for distance changing between collimating system 2 and window 19 of position-sensitive detector 1;
guide slots 10 in mounting plate 3 for parallel displacement of collimating system 2 relative to window 19 of position-sensitive detector 1.

FIG. 1B shows sectional view of collimating system 2. On this figure: 31—channels rows; 32—the middle row of channels; 33—a plane of a section passing through the middle row 32; 34—the central channel in the said middle row; 35—an axial line of the central channel 34; 11—an axis, which lies in the plane 33 passing through the middle row 32; this axis is perpendicular to the central channel 34; 7—an axis, perpendicular to the plane 33.

Collimating system 2 is made in the form of honeycomb structure (FIG. 2) comprising multitude of tubular channels for transmittance of diffracted X-ray radiation. Walls of adjacent tubular channels 16 are fused together.

If a dimension of the window of position-sensitive detector 1 in transverse direction (its width) is small in comparison with its length, then it is possible to build collimating system 2 with outlet end face 22 and inlet end face 23 in the form of coaxial cylindrical surfaces (FIG. 3, variant "a"). At that, dimension of outlet end face 22 is close to that of window of the position-sensitive detector. Tubular channels 16 in this case are oriented by radii of said cylindrical surfaces, and collimating system has a linear focus 24 situated on common axis of these surfaces.

However, better results, especially in case of larger window width of the position-sensitive detector, may be obtained by using collimating system having point focus, with outlet and inlet end faces in the form of concentric spherical surfaces (FIG. 3, variant "b"), and longitudinal axes of tubular channels oriented by radii of this spherical surface and their extensions intersecting in focus 24.

In both above embodiments of collimating system focusing, one or both of its end faces may be planar, as shown in FIG. 3, variant "c", which depicts planar and parallel to one another outlet 22 and inlet 23 end faces. Such collimating system may be represented as kind of "truncated" collimating system with cylindrical or spherical end faces.

Tubular channels have rectilinear longitudinal axes and converge towards inlet end face 22 of the collimating system. In particular, they are shaped as truncated cone or pyramid, with lesser bases forming inlet end face of collimating system. At that, said cone does not have to be circular, and pyramid—a regular one. Tubular channels are oriented with their outlet ends, forming outlet end face 22 of collimating system, towards window 19 of the position-sensitive detector (FIG. 1A). Outlets of tubular channels in the outlet end face 22 of collimating system 2 are arranged in several rows, oriented along window 19 of the position-sensitive detector 1. Number of said rows determines dimension of collimating system in transverse direction and depends on the window width of the position-sensitive detector 1. It should be such as to ensure the uttermost utilization of window area of the position-sensitive detector.

Collimating system in the form of said honeycomb structure having required configuration may be made, in particular, of glass, by using technology for polycapillary structures production, similar to that disclosed in patent of Russian Federation No. 2096353, publ. 20 Nov. 1997 [3].

In order to ensure collimating properties of the produced honeycomb structure with tubular channels, glass tubes or glass capillaries or polycapillaries made of lead glass, or those having internal walls coating made of lead or other heavy metal absorbing X-ray radiation, may be used as source material in realization of said technology.

If tubular channels of the produced polycapillary system 2 meet the conditions:

$$D/H > \theta_c$$

$$\theta_c = \hbar \omega_p / E,$$

where D and H denote, correspondingly, the largest transverse dimension of a separate tubular channel and its length, $\theta_c$ is a critical angle of total external reflection of X-ray radiation from channel walls material, $\hbar$ is Planck constant, $\omega_p$ denotes plasma frequency of the material of tubular channels walls, and E denotes quantum energy of X-ray radiation used, than due to multiple total external reflection, a possibility is excluded of transmission to the channel's end of rays having at the inlet of the tubular channel a deviation from its longitudinal axis, not exceeding $\theta_c$.

It is seen in FIG. 4, which illustrates the case of focus 24 of the collimating system being situated inside the specimen studied 15, in what manner occurs "screening" of "extraneous" rays in the plane of diffraction angle. Such a ray, crossed-out in the drawing, will not enter any of tubular channels 16 and, therefore, may not cause distortion of the diffractogram obtained.

X-ray tube 12 (FIG. 5) and X-ray half-lens 13 generate parallel primary X-ray beam 14. This beam, being reflected in specimen 15 studied from unlike crystallographic planes hkl and HKL having normals N1 and N2, at angles Θ1 and Θ2, correspondingly, gives rise to diffracted X-ray beams from the planes hkl and HKL. Diffracted beams, on coming selectively through collimating system 2, are registered with position-sensitive detector 1.

For X-ray phase analysis, the X-ray tube 12 and X-ray half-lens 13 are placed and fastened securely at an angle of 45° to the surface of specimen studied 15, or at other angle, determined by the purpose of investigations, depending on the anode material of X-ray tube 12. The specimen studied 15 is positioned for X-ray phase analysis in such a way as to place the largest possible portion of its surface in reflecting position. To do this, in particular, rotation is used of the specimen studied 15 around axis perpendicular to its surface (see: Portable Parallel Beam X-ray Diffraction System θ/θ Diffractometer, STOE News, STOE&CIE, 2003, S. 1–28, [4]).

For X-ray analysis of crystal lattice parameters of the material, an effort is made to shape as narrow as possible parallel beam 14 with X-ray half-lens 13, while specimen studied 15 is left motionless. X-ray tube 12 and half-lens 13 are placed at an angle to the surface of specimen studied 15, which is equal to diffraction angle Θ1 for hkl planes most important for investigations (see: A Convergent Beam, Parallel Detection X-Ray Diffraction System for Characterizing Combinatorial Epitaxial Thin Films. K. Omote, T. Kikuchi, J. Harada, V. Kawasaki. The Rigaku Journal, Vol. 18, No. 1, 2001, pp. 34–41 [5]).

For X-ray analysis of stress-deformed state, X-ray tube 12 with half-lens 13 is positioned for measurements in the range of large diffraction angles Θ in such a way that beam 14 would be incident at an angle of 60° to 80° to the surface of the specimen 15 studied (see: S. S. Gorelik, Yu. A. Skakov, L. N. Rastorguev, Rentgenovskiy i elektronno-opticheskiy analiz (X-ray and electron-optical analysis), Moscow, MISIS, "Nauka" publishers, 2002, p. 17–122 [6] (in Russian)).

For X-ray analysis of preferred orientations (textures) by parallel beam method, X-ray tube 12 with half-lens 13 is positioned for shaping of beam 14 at an angle of 45° to the surface of specimen studied 15.

Parallel primary X-ray beam 14 irradiates a portion of surface of the polycrystalline specimen studied 15 comprising, at the minimum, M regions of coherent X-ray scattering. Of M coherent scattering regions, m are situated in reflecting position of crystallographic plane systems having unlike indices (hkl and HKL). These systems have different interplanar spacing and are aligned at different angles to parallel primary X-ray beam of λ wavelength, corresponding to reflection angles in Bragg equation (2d sin Θ=nλ).

Each of m regions of coherent scattering reflects narrow parallel X-ray beam (having greater divergence than that incident, because region of coherent scattering itself is a selector of radiation with different wavelength, and primary beam carries α- and β-components of K-series of characteristic X-ray radiation) at an angle, corresponding to interplanar distances of planes, reflecting in the given region of coherent scattering.

If the reflecting region was a mathematical point, as in the case of "ideal polycrystal", then infinitely narrow parallel beams would diverge radially from this point by generatices of diffraction cones (in FIG. 5, which represents a section of three-dimensional diffraction pattern, by straight lines, outgoing from intersection point of N1 and N2 normals to the reflecting planes hkl and HKL; primary X-ray beam 14 being infinitely narrow in the direction perpendicular to drawing plane). As a matter of fact, even in this model, double Bragg reflections would be present ("Borrmann fan"), which would increase the width of interference line of diffractive reflection even on reflection diffractograms due to finite depth of half-value layer (see: D. K. Bowen, B. K. Tanner. High-resolution X-ray diffractometry and topography. Sankt-Peterburg, Nauka publishers, 2002, p. 31–60, 95–96 [7] (Russian translation).

Actually, irradiated area has finite geometrical dimensions, and the detecting unit proposed solves following problems:

- transmittance and registration of all X-rays, passing in axial direction of tubular channels, from as large irradiated area as possible, utilizing greatest possible area of detector window without its being overlapped with a slit;
- interception of all other secondary X-rays, whether reflected or those generated due to fluorescence, on their way to the window of position-sensitive detector;
- removal of the requirement, mandatory in schemes [4]–[5], as to monochromatization of primary X-ray beam, which decrease intensity of the primary beam by 12–15 times;
- increase in radiation intensity captured by the position-sensitive detector and provision of additional instrument for researcher in the form of second wavelength (energy space between $K_\alpha$-radiation and $K_\beta$-radiation are known for all metals employed as anodes in X-ray tubes), which is so often missing with monochromatization of the primary beam.

FIG. 6 shows position of the collimating system 2 focused on surface of the specimen studied 15. Outlet window 22 of the collimating system has equal distances 17 and 18 to the detector 1. Axes of tubular channels of the collimating system 2 converge in a point focus 24 on surface of the specimen studied 15.

In order to provide comparative performance evaluation of the detecting unit proposed and that known from [2], diffractograms of tungsten carbide (WC) have been registered, which are demonstrated in FIG. 7. In measurements scheme, shown in FIG. 5, X-ray tube with copper anode has been used. The diffractogram "A" shown in FIG. 7 represents a diffraction pattern registered using the detecting unit of a design known from [2], and diffractogram "B" in FIG. 7—that using the detecting unit proposed. Obviously perceptible effects include lowering of background level, decrease in the width of X-ray interference peaks and resolution increase ("peak-background" ratio). Obviously, partial filtration takes place of component of the primary X-ray beam radiation 14.

By varying the position of collimating system 2 and its orientation angles relative to detector 1, selective transmission may be achieved (FIG. 8) of α- and β-components of the primary X-ray beam. In this case, focus 24 of tubular channels of the collimating system 2 moves below the surface of the specimen studied 15. Regions of coherent scattering themselves divide α- and β-components of the primary parallel beam 14 by their reflection angle. By moving the collimating system 2 from position 2.1 into position 2.2, an angle range may be passed over, in which either both α- and β-components of diffracted beam will be transmitted to the outlet of collimating system (variant "a" at the bottom of FIG. 8), or only β-component (variant "b") or only α-component (variant "c"). It is impossible to achieve this in the primary beam with no collimating systems whatever, except for diffraction (use of monochromators).

FIG. 9 shows displacement of the collimating system 2 along the axis of one of its central tubular channels while keeping equal changes in distances 17 and 18 to the position-sensitive detector 1. At that, in spite of decrease in the number of tubular channels taking part in the work of the collimating system 2, information collected comes from greater area of the specimen studied 15, than in the case illustrated in FIG. 6. Increase of this displacement towards surface of the specimen studied 15 (FIG. 10) results in still greater contraction of angular capture region of reflected rays by the position-sensitive detector 1. For small diffraction angles, nontransmitting region of the collimating system 2 increases, however, for large diffraction angles (left part of position-sensitive detector 1) conditions of transmittance improve. Such arrangement of collimating system is most applicable to X-ray testing of stressedly deformed state of materials.

Rotations of collimating system 2 about axis 7 (FIG. 1B) perpendicular to the middle row of tubular channels are shown in FIG. 11 and FIG. 12. These rotations are performed in planes of drawings in FIG. 11 and FIG. 12 clockwise and counterclockwise, correspondingly.

Rotation of collimating system 2 towards to small-angle diffraction (FIG. 11) results in increased intensity and improved resolution of X-ray diffraction interference peaks in this region (see FIG. 13, the difractogram "a").

Maximum transmittance of X-rays by collimating system 2 is achieved by rotation of the collimating system about axis 11 (see FIG. 14) lying in a plane passing through the middle one of tubular channels rows, and perpendicular to central tubular channel in said row (FIG. 1B), so as to increase as much as possible capture angle Ω of diffracted radiation with full width of window 19 of the position-sensitive detector 1 in Δ2Θ range of detection angles.

Rotation the collimating system in opposite direction (towards larger diffraction angles) results in intensity redistribution between interference peaks of the diffraction with increase in intensity and resolution in the large angles region (see FIG. 13, the difractogram "b"). This pattern is strengthened on further rotation (see FIG. 13, the difractogram "c"). One can see good resolution of peaks in the right part of diffractogram (range of large diffraction angles). The possibility described of adjusting the resolving power of diffractogram in the desired range of diffraction angles represents one more important feature of the detecting unit proposed.

Possibility to place different angular ranges of the interference pattern in unequal conditions in one exposure allows comparing X-ray pictures containing in different, by conditions of their registration, databases. To this end, it is enough preliminarily to calibrate the collimating system by reference substance. By simulating diffraction pattern of interference, obtained using Debye chambers, with "Θ–2Θ"-diffractometers having different focusing arrangements and "Θ—Θ"-diffractometers by parallel beam method, all databases accumulated in X-ray crystallography may be used.

In recent years, two-coordinate position-sensitive detectors are employed to an increasing extent in X-ray diffractometry, especially in those fields where due to the complex structure of the object investigated use of single-coordinate detectors is associated with multiple exposure (see: V. Kahenberg, C. S. J. Shaw and J. B. Parrise. Crystal structure analysis of sinthetic $Ca_4Fe_{1.5}Al_{17.67}O_{32}$: A high-pressure, spinel-related phase, American Mineralogist, Vol. 86, pp. 1477–1482, 2001 [8]). Two-coordinate position-sensitive detector may also be used in the detecting unit proposed, furnished with collimating system in the form of specified honeycomb structure, located in front of the window of position-sensitive detector.

Thus, utilization of the proposed detecting unit provides for:

registration of X-ray radiation obtained from larger irradiated area of the specimen studied and maximum utilization of window area of the position-sensitive detector;

interception of all "extraneous" secondary X-rays, whether reflected or generated due to fluorescence, on their way to the window of position-sensitive detector;

elimination of the necessity in monochromatization of primary beam and consequent increase in the intensity of radiation acting on position-sensitive detector;

realization of possibilities, provided by use of second wavelength, which are absent in case of monochromatization of the primary beam;

adjustment of resolving power of diffractogram in desired region of the diffraction angles range studied;

acquisition of diffractograms, suitable for comparison with those taken from different databases created in roentgenography.

Photographs of working specimen of the detecting unit proposed (with removed position-sensitive detector), with collimating system 2 having coaxial cylindrical outlet 23 and inlet 23 end faces, are shown in FIG. 15.

REFERENCES

1. D. A. Goganov, B. S. Losinsky, N. B. Tsvetova, T. P. Toporkova. Sealed-off proportional X-ray emission counter SPRO-12.—In: Apparatura i metody rentgenovskogo analiza (Equipment and methods for X-ray analysis). Leningrad, Mashinostroenie editing house, 1972, Issue 11, pp. 151–155 (in Russian).
2. Ortendahl D., Perez-Mendez V., Stoker J. One dimensional curved wire chamber for powder X-ray crystallography.—Nucl. Instrum. And Meth., 1978, Vol. 156, No. 1–2, pp. 53–56.
3. Patent of Russian Federation No. 2096353 (publ. 20 Nov. 1997).
4. Portable Parallel Beam X-ray Diffraction System θ/θ Diffractometer. STOE News, STOE&CIE, 2003, S. 1–28.
5. A Convergent Beam, Parallel Detection X-Ray Diffraction System for Characterizing Combinatorial Epitaxial Thin Films. K. Omote, T. Kikuchi, J. Harada, V. Kawasaki. The Rigaku Journal, Vol. 18/No. 1/2001/pp. 34–41.
6. S. S. Gorelik, Yu. A. Skakov, L. N. Rastorguev, Rentgenovskiy i elektronno-opticheskiy analiz (X-ray and electron-optical analysis), Moscow, MISIS, "Nauka" publishers, 2002, pp. 17–122 (in Russian).
7. D. K. Bowen, B. K. Tanner. High-resolution X-ray diffractometry and topography. Sankt-Peterburg, Nauka publishers, 2002, p. 31–60, 95–96 (Russian translation).
8. V. Kahenberg, C. S. J. Shaw and J. B. Parrise. Crystal structure analysis of sinthetic $Ca_4Fe_{1.5}Al_{17.67}O_{32}$: A high-pressure, spinel-related phase, American Mineralogist, Vol. 86, pp. 1477–1482, 2001.

The invention claimed is:

1. Detecting unit for X-ray diffraction measurements, comprising:
a position-sensitive detector and
a collimating system located in front of a window of the detector,
said collimating system being in a form of a honeycomb structure comprising multiple tubular channels for transmittance of diffracted X-ray radiation,
adjacent tubular channels of said multiple tubular channels having walls fused together,
the tubular channels converging towards inlet end face of said collimating system and having outlet ends forming outlet end face of said collimating system directed towards the window of said position-sensitive detector, the tubular channels having rectilinear longitudinal axes,
the outlets of the tubular channels in said outlet end face of said collimating system being arranged in several rows along the window of said position-sensitive detector,
said walls of the tubular channels being made of material absorbing X-ray radiation, or having a coating of such material,
the detecting unit further comprising an adjusting mechanism for adjusting position of the collimating system relative to the window of said position-sensitive detector,
the adjusting mechanism being configured for providing rotation of the collimating system around an axis perpendicular to a plane passing through a middle row of the rows of the tubular channels.

2. Detecting unit according to claim 1, wherein:
the outlet end face of the collimating system is in a form of a cylindrical surface, and
the tubular channels being oriented along radii of said cylindrical surface, axis of which corresponds to a linear focus of the collimating system.

3. Detecting unit according to claim 2, wherein the inlet end face of said collimating system has a form of cylindrical surface coaxial with respect to the cylindrical surface at the outlet end face.

4. Detecting unit according to claim 1, wherein:
the outlet end face of the collimating system has a form of a spherical surface, and
the tubular channels have longitudinal axes oriented along radii of said spherical surface.

5. Detecting unit according to claim 4, wherein the inlet end face of said collimating system has a form of spherical surface concentric with respect to the spherical surface at the outlet end face.

6. Detecting unit according to claim 1, wherein:
the collimating system has planar and parallel to one another surfaces at said outlet and inlet end faces, and
extensions of longitudinal axes of said tubular channels intersect in a point corresponding to a focus of the collimating system and being on a line perpendicular to said planar surfaces and passing through a geometrical center of said outlet or inlet end faces.

7. Detecting unit according to claim 1, wherein:
the collimating system has planar, parallel to one another surfaces at the outlet and inlet end faces, and
longitudinal axes of the tubular channels are oriented along radii of coaxial cylindrical surfaces having a common axes corresponding to a linear focus of the collimating system.

8. Detecting unit according to any of claims 1 to 7, wherein the adjusting mechanism is configured for providing linear displacement of the collimating system in a direction of a longitudinal axis of one of said tubular channels arranged in a central zone of the collimating system.

9. Detecting unit according to claim 8, wherein the adjusting mechanism is further configured for providing rotation of the collimating system around an axis in a plane passing through a middle row of the row of the tubular channels, said axis being perpendicular to a central tubular channel in said row.

10. Detecting unit according to claim 9, wherein the greatest transverse dimension D of a separate tubular channel and its length H satisfy relationship: $D/H > \theta_c$, where $\theta_c$ denotes critical angle of total external reflection of X-ray radiation from material of channel walls.

11. Detecting unit according to any of claims 1 to 7, wherein the adjusting mechanism is configured for providing rotation of the collimating system around an axis in a plane passing through a middle row of the rows of the tubular channels, said axis being perpendicular to a central tubular channel in said row.

12. Detecting unit according to any of claims 1 to 7, wherein the greatest transverse dimension D of a separate tubular channel and its length H satisfy relationship: $D/H > \theta_c$, where $\theta_c$ denotes critical angle of total external reflection of X-ray radiation from material of channel walls.

* * * * *